United States Patent [19]

Schwan

[11] 4,210,761

[45] Jul. 1, 1980

[54] 1-(4-CHLOROPHENYL)-3-(2,2-DIETHOXYETHYL)-2-IMIDAZOLIDINONE

[75] Inventor: Thomas J. Schwan, Norwich, N.Y.

[73] Assignee: Morton-Norwich Products, Inc., Norwich, N.Y.

[21] Appl. No.: 51,514

[22] Filed: Jun. 25, 1979

[51] Int. Cl.² ............................................. C07D 233/34
[52] U.S. Cl. ................................. 548/320; 424/273 R
[58] Field of Search ........................................ 548/320

[56] References Cited

U.S. PATENT DOCUMENTS 3,905,996  9/1975  Perronnet ............................. 548/320

OTHER PUBLICATIONS

Wright et al., J. Med. Chem., 1966, vol. 9, pp. 852–857.

*Primary Examiner*—Natalie Trousof
*Attorney, Agent, or Firm*—Anthony J. Franze

[57] ABSTRACT

The compound of the formula:

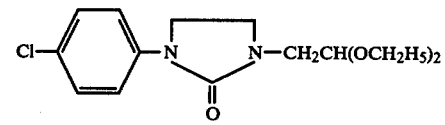

is useful as an antifungal agent.

1 Claim, No Drawings

1-(4-CHLOROPHENYL)-3-(2,2-DIETHOXYETHYL)-2-IMIDAZOLIDINONE

This invention is concerned with chemical compounds. In particular, it is concerned with a compound of the formula:

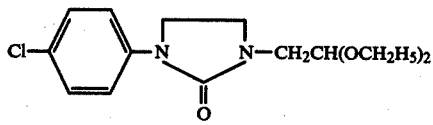

This compound is useful as an antifungal agent. At concentrations of 100 μg/ml in Sabouraud's dextrose broth it inhibits the growth of *Microsporum canis* in the commonly employed agar diffusion test. It is adapted to be combined in various forms such as elixirs, dusts, unguents, solutions and suspensions to provide compositions inimical to fungal growth.

In order that this invention may be readily available to and understood by those skilled in the art, the following example is appended:

A 50.0 g (0.25 mole) portion of 1-(4-chlorophenyl)-2-imidazolidinone in 1750 ml of dimethylformamide was treated with 40.6 g (1.02 moles) of NaH (60% in mineral oil), 38.2 g (0.25 mole) of NaI and 100.0 g (0.51 mole) of bromoacetaldehyde diethylacetal. The reaction mixture was then heated at 70°–75° for 24 hours, cooled to room temperature, poured into 10 l. of cold $H_2O$, stirred for 0.2 hour and filtered. The white solid was washed with 1000 ml of $H_2O$ and air dried, m.p. 58°–59°; wt. 56 g (72%).

An analytical sample, m.p. 63°–65°, was obtained by recrystallization from heptane.

Anal. Calcd. for $C_{15}H_{21}ClN_2O_3$: C, 57.59; H, 6.71; N, 8.95. Found: C, 57.50; H, 6.80; N, 8.98.

What is claimed is:
1. The compound 1-(4-chlorophenyl)-3-(2,2-diethoxyethyl)-2-imidazolidinone.

* * * * *